(12) United States Patent
Chang et al.

(10) Patent No.: US 8,951,557 B2
(45) Date of Patent: Feb. 10, 2015

(54) SUSTAINED RELEASE SOLID FORMULATIONS AND METHODS OF MANUFACTURING THE SAME

(75) Inventors: Shajoung Chang, Yongin-si (KR); Oak Choi, Suwon-si (KR)

(73) Assignee: Hana Pharm. Co. Ltd., Hwasung-si (KR)

( * ) Notice: Subject to any disclaimer, the term of this patent is extended or adjusted under 35 U.S.C. 154(b) by 655 days.

(21) Appl. No.: 12/867,935

(22) PCT Filed: Apr. 28, 2008

(86) PCT No.: PCT/KR2008/002391
§ 371 (c)(1),
(2), (4) Date: Aug. 17, 2010

(87) PCT Pub. No.: WO2009/104838
PCT Pub. Date: Aug. 27, 2009

(65) Prior Publication Data
US 2011/0008424 A1 Jan. 13, 2011

(30) Foreign Application Priority Data

Feb. 18, 2008 (KR) ........................ 10-2008-0014290

(51) Int. Cl.
*A61K 9/58* (2006.01)
*A61K 9/16* (2006.01)
*A61K 9/18* (2006.01)
*A61K 31/485* (2006.01)
*A61K 9/26* (2006.01)
*A61K 9/20* (2006.01)

(52) U.S. Cl.
CPC ............. *A61K 9/2013* (2013.01); *A61K 9/2095* (2013.01); *A61K 31/485* (2013.01); *A61K 9/2009* (2013.01); *A61K 9/2068* (2013.01); *A61K 9/2027* (2013.01)
USPC ........... 424/462; 424/458; 424/465; 424/486; 514/282; 546/45

(58) Field of Classification Search
None
See application file for complete search history.

(56) References Cited

U.S. PATENT DOCUMENTS

| | | | |
|---|---|---|---|
| 6,290,990 | B1 | 9/2001 | Grabowski et al. |
| 2002/0044968 | A1* | 4/2002 | van Lengerich ............. 424/469 |
| 2003/0035835 | A1 | 2/2003 | Bartholomaeus et al. |
| 2003/0180359 | A1* | 9/2003 | Vergnault et al. ............ 424/468 |
| 2008/0248107 | A1* | 10/2008 | Pilgaonkar et al. ........... 424/458 |

FOREIGN PATENT DOCUMENTS

| | | |
|---|---|---|
| EP | 1187601 B1 | 7/2005 |
| WO | 9310765 A1 | 6/1993 |
| WO | 03101384 A2 | 12/2003 |
| WO | WO 2007052299 A2 * | 5/2007 |

OTHER PUBLICATIONS

Dakkuri et al., "Sustained Release from Inert Wax Matrixes III: Effect of Povidone on Tripelennamine Hydrochloride Release", Journal of Pharmaceutical Sciences, Mar. 1978, pp. 357-360, vol. 67, No. 3.
Zhang et al., "Melt Granulation and Heat Treatment for Wax Matrix-Controlled Drug Release", Drug Development and Industrial Pharmacy, 2003, pp. 131-138, vol. 29, No. 2, Marcel Dekker, Inc., New York, NY.
Reza et al., "Comparative evaluation of plastic, hydrophobic and hydrophilic polymers as matrices for controlled-release drug delivery", J Pharm Pharmaceut Sci, 2003, pp. 282-291, vol. 6, No. 2.
Rao, Monica R. P., "Effect of processing and sintering on controlled release wax matrix tablets of ketorolac tromethanine", Indian Journal of Pharmaceutical Sciences, 2009, pp. 538-544, vol. 71, Issue 5.

* cited by examiner

*Primary Examiner* — H. Sarah Park
(74) *Attorney, Agent, or Firm* — The Webb Law Firm

(57) ABSTRACT

Disclosed are a sustained release solid formulation comprising a drug, for example, oxycodone or its pharmaceutically acceptable salt, in a water-insoluble matrix, which comprises a wax type excipient and copovidone, and thus, has increased compressibility and fluidity and reduced adhesiveness, and a method of preparing the same.

10 Claims, 1 Drawing Sheet

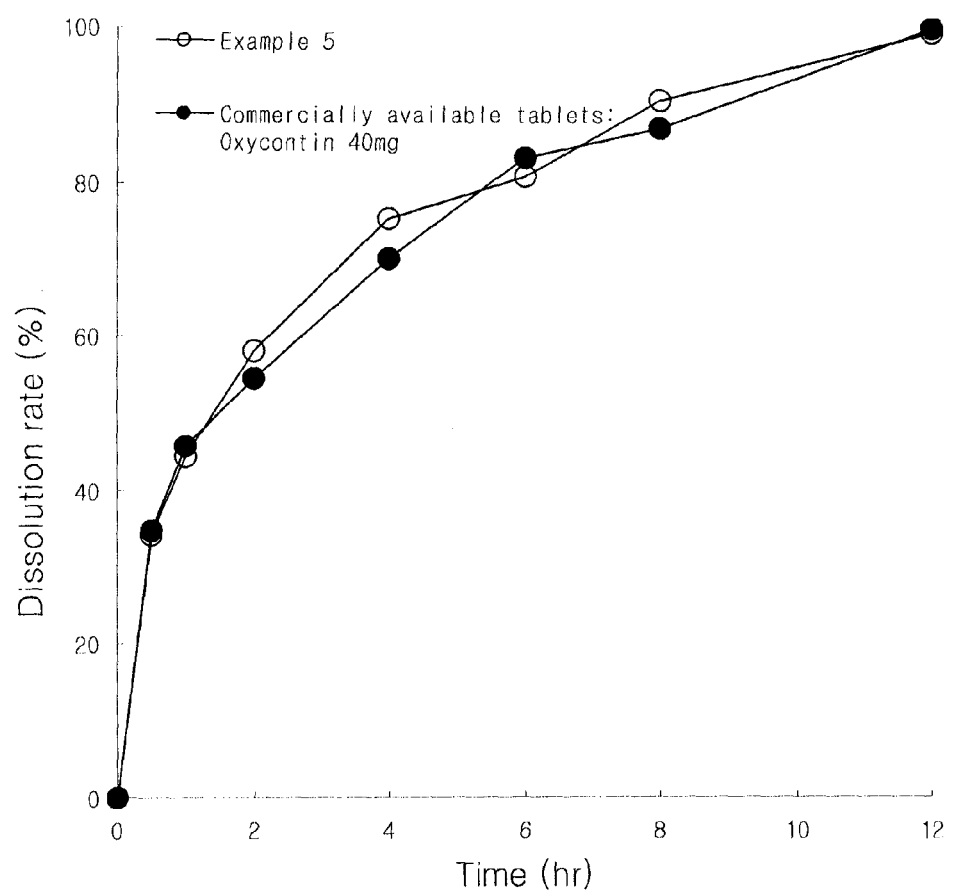

SUSTAINED RELEASE SOLID FORMULATIONS AND METHODS OF MANUFACTURING THE SAME

TECHNICAL FIELD

The present invention relates to a sustained release solid formulation and a method of preparing the same, more particularly to a sustained release solid formulation comprising a drug in a water-insoluble matrix, which comprises a wax type excipient and copovidone, and thus, has increased compressibility and fluidity and reduced adhesiveness, and a method of preparing the same.

BACKGROUND ART

As compared with rapid release formulations, sustained release formulations release a drug continuously over an extended period of time inside the body. Thus, they can keep effective plasma level of the drug for a long time, and so reduce variance in plasma level from frequent administration of the formulation and side effects therefrom. Further, they can improve compliance from the reduced number of administration.

Various techniques are used to prepare sustained release formulations with high effectiveness and safety. Among them, the sustained release matrix tablet is known as a formulation that can be prepared in the simplest manner. Sustained release matrix tablets are frequently used in the pharmaceutical industry because they can be produced using common techniques and apparatuses. Depending on the excipient used, they are classified into water-soluble and water-insoluble matrix tablets. Water-soluble matrix tablets are of the type in which the matrix is slowly dissolved from the outside in the gastrointestinal fluid and the drug is released. Examples of such matrices include hydrophilic polymers, such as hydroxypropyl cellulose (HPC), hydroxypropyl methylcellulose (HPMC), polyvinyl alcohol (PVA), Carbopol, polyethylene oxide (POE), etc. Water-insoluble matrix tablets include ones made from waxes such as hydrogenated castor oil or synthetic resins such as ammonio methacrylate copolymer (Eudragit). The water-insoluble matrix tablets are characterized in that they have no change in appearance while the drug is slowly released over a long period of time, but the drug is released through pores from the inside of the matrix. They are advantageous over the water-soluble matrix tablets in that the drug is slowly released over a given time, which is less affected by the gastrointestinal motility.

Recently, the technique of preparing sustained release formulations using a wax is drawing a great attention. In particular, as various wax type pharmaceutical excipients are developed, a variety of techniques for preparing sustained release formulations using waxes have become available. These techniques share the common feature to use a high fusibility of the wax. Typically, various methods are used, such as melt extrusion, melt granulation, melting or dissolving a wax in an adequate solvent followed by coating the solution on the surface of particles, and dispersing a drug in a melted wax followed by compressing the dispersion into tablets.

Alternatively, a wax is not melted but employed in wet granulation or direct compression together with other excipients to manufacture tablets. However, when compressing granules or other compositions including wax into tablets, such problems as insufficient compressibility or surface adhesion may occur when they contain a high weight percentage of wax. As a result, fluidity of particles in the hopper may be remarkably decreased during tabletting, and they may severely adhere to the punch, thereby resulting in severe problems in practical manufacture. Such adhesion can be prevented to some extent by adding a lubricant, but it is usual to limit the content of a lubricant no more than 5% of the total weight of granules. This is because excessive use of the lubricant may result in capping or laminating during the tabletting. Actually, from the above-mentioned problems, the content of a wax type excipient in compositions is generally limited to below 30% when preparing tablets by wet granulation or direct compression with the wax type excipient. Therefore, only the addition of lubricant would not be sufficient to solve the adhesion of wax containing granules or other compositions in practical manufacture.

Copovidone (copolyvidone; vinylpyrrolidone-vinyl acetate (VP/VAc) copolymer; 60/40) was marketed in 1975 under the trade name of Luviskol® VA 64. In Europe and other countries, it has been utilized in the pharmaceutical industry for more than a decade. However, researches thereon and its applications in cosmetics and others have been just recently ongoing actively. At present, copovidone is marketed under the trade names of Kollidon® VA 64 (by BASF) and Plasdone S-630 (by ISP), and used as a binder, a coating agent and for sustained release formulations in the pharmaceutical industry.

Especially, it is used as a binder providing good coherence for tablets and granules, and generally used at an amount of 2-5% in granules. According to the data supplied by BASF, its copovidone has a much higher plasticity than povidone (polyvinylpyrrolidone) K-30, and thus, prevents capping during tabletting and reduces friability of manufactured tablets.

From the above properties of copovidone, it is used as a binder for direct compression of incoherent compositions.

While applicable in wet granulation, it can be also used as dissolved in water or alcohol and prepared into a binding solution, or as added to a kneading solution in a mixture with other excipients to prepare granules. Copovidone has been shown to have a low hygroscopy. When kept at RH 80% for 7 days, Kollidon® VA 64 absorbs less than 20% of water, which corresponds to less than ⅓ of Kollidon 30 (povidone K-30).

Especially, adhesion to a punch can be remarkably reduced during tabletting under a wet condition. However, in the manufacture of matrix type sustained release formulations using wax type excipients, researches on any synergic effect of copovidone and wax type excipient for the maintenance of adequate drug dissolution rate and for the prevention of adhesion of the wax to a punch and capping during tabletting have not yet been reported.

Oxycodone is an opioid analgesic that directly binds with the opioid receptor to provide analgesic effect. Since 1917, it has been clinically used for patients with moderate to severe pain. At first, oxycodone was administered by injection. Later, as it was found that it can be absorbed rapidly even when administered orally, it began to be used as an oral solution, and then, manufactured into a rapid release tablet containing 5 mg of oxycodone. Recently, not only the US, but also many other countries including Korea adopt the Biopharmaceutics Classification System (BCS) and provide the ground of exemption from the in-vivo bioequivalence test. It is because the in-vivo behavior of a drug can be predicted from the in-vitro dissolution profile once the drug's BCS class is known. Especially, the in-vivo behavior of the drugs belonging to the BCS class I can be expected from their in-vitro profile and pharmacokinetic parameters. Oxycodone hydrochloride has a high solubility and is rapidly absorbed to the body when administered orally. Its bioavailability is 60-87% as compared to that of direct administration into bloodstream. However, AUC and $C_{max}$ increase in proportion to the administration amount within a certain range. Although oxycodone hydrochloride is not explicitly listed in the BCS class I, the drug exhibits a linear in-vivo behavior, showing the rapid absorbance at a constant rate upon dissolution, and so is considered the closet to class I of the four BCS classes.

Therefore, from such in-vivo parameters as absorption rate constant, elimination rate constant, etc. of prior injections or rapid release tablets, the drug's in-vivo behavior can be expected easily in designing its sustained release formulation. Usually, the analgesic effect of oxycodone hydrochloride sustains for 4 to 6 hours when a 5 mg rapid release tablet is administered. Clinically, it has to be usually taken 4 times a day. This causes problems for the regular medication, one of important rules in management of pains, for cancer patients. Further, too fast release of the drug associated with the administration of a rapid release tablet causes a high initial blood level and may lead to such side effects as respiratory depression, which are commonly expressed with opioid analgesics. To solve these problems, researches have been carried out on a sustained release formulation that slowly releases oxycodone and maintains an effective plasma level over an extended period of time. For example, WO 93/10765 discloses a controlled release oxycodone formulation prepared by coating the drug with an acrylic excipient for sustained release such as Eudragit to prepare granules and then coating the granules with melted stearyl alcohol. The formulation uses two kinds of excipients for sustained release and controls the drug release in two phases.

This formulation comprises 10, 20 or 40 mg of oxycodone per tablet and is marketed under the trade name of OxyContin® and instructed to be administered twice a day. This product is characterized in that it has a two-phase release profile with two different release rates during 12 hours. In addition, WO 2003/101384 discloses a sustained release formulation of oxycodone hydrochloride to be administered once per 24 hours.

This formulation for administration once a day is to improve that OxyContin® for administration twice a day provides two consecutive peaks and troughs a day. This formulation is characterized in that it includes a rapid-release part and a controlled-release part. The controlled-release part is formed by coating a double-layer tablet consisting of a drug core layer and a push layer comprising an osmotic agent, so that the drug is released slowly through a semipermeable membrane.

Then, the rapid-release composition comprising the drug of a low dose, for example, 1 mg per 20-mg tablet, is coated on the surface of the controlled-release part, and finally, such an agent as Opadry® (Colorcon, USA) is film coated thereon.

This formulation is characterized in that a 0-order dissolution pattern is attained during the drug release. This formulation shows a lag time before the drug is released from the double layers through the semipermeable membrane. The low dose rapid-release layer seems to have been introduced to prevent the retardation of drug release. As a result, it can provide the sustained drug release over 24 hours while showing a fast analgesic effect in the patient's body without delay.

However, because a lot of process parameters have to be controlled in practical production, the production efficiency is decreased. In addition, because a multi-step preparation process is required, there may be a wide range of variances in product dissolution rates, which is a frequent problem in the production of sustained release formulations.

DISCLOSURE

Technical Problem

The present inventors have carried out extensive researches in order to develop a sustained release solid formulation which enables the control of release using a single excipient for sustained release while using a small amount (weight %) of additives with respect to the total weight of unit dosage form, and can be produced in a simple manner to improve production efficiency and slowly release the drug effectively over a long period of time. As a result, they found out that, by using a wax as an excipient for sustained release in combination with copovidone as a binder, a mixture or granules for a sustained release solid formulation, which provides increased compressibility and fluidity and reduced adhesiveness, can be obtained, the mixture or granules can be easily compressed using a high speed tabletting machine, and the resultant solid formulation exhibits excellent sustained release effect.

Accordingly, an object of the present invention is to provide a solid formulation which can be prepared simply with a high production efficiency with a small amount of additives based on the weight of unit dosage form, and can release a drug effectively and slowly over a long period of time while reducing variances in dissolution patterns between production lots.

Another object of the present invention is to provide a method of preparing the solid formulation.

Technical Solution

One aspect of the present invention provides a sustained release solid formulation comprising a drug in a water-insoluble matrix, wherein the water-insoluble matrix comprises a wax type excipient and copovidone, and has the void filled or the surface coated with the wax and the porosity reduced by the wax and the copovidone.

Another aspect of the present invention provides a method of preparing a sustained release solid formulation, which comprises:

i) mixing a drug with a wax type excipient to prepare a mixture or granules;

ii) heating the mixture or granules of step i) to a temperature at which the wax type excipient can be melted, and then cooling the heated mixture or granules; and iii) compressing or filling in a capsule the mixture or granules of step ii), wherein copovidone is added in any of steps i), ii) and iii).

DESCRIPTION OF DRAWINGS

The above and other objects, features and advantages of the present invention will be more clearly understood from the following detailed description taken in conjunction with the accompanying drawing in which:

FIG. 1 is a graph showing the dissolution test results of tablets at pH 6.8 [○: formulation of Example 5; ●: commercially available formulation (OxyContin® sustained release tablet)].

BEST MODE

Hereinafter, the present invention is described in further detail.

The present invention is to provide a sustained release solid formulation which can be produced in a simple manner and provides a highly reproducible dissolution rate. For this purpose, prescriptions for a sustained release formulation were designed with reference to the in-vivo pharmacokinetic behavior of the prior rapid release tablets of oxycodone hydrochloride as a model drug. Although the prior rapid release tablets have many disadvantages upon administration, they have been confirmed from decades of experience to give a plasma level within the range of therapeutic dose with which the pain can be controlled. In general, 5-mg rapid release tablets are administered 4 times a day. The administration interval is 6 hours, and the lowest plasma level $C_{ss,min}$ and the highest plasma level $C_{ss,max}$ in a steady state would fall within the range of therapeutic dose providing a suitable pharmacological effect. Especially, the drug belonging to the class I like oxycodone, having a linear pharmacokinetic parameter, for example, provided that the drug is completely released to the body within 12 or 24 hours, $AUC_{ss}$ is not significantly different from that of the rapid release tablet, given the same daily dose. This assumption was proven by the commercially available oxycodone product, as described in Physicians' Desk Reference, 57th Ed. pp. 2851-2856 (2003). The present invention is to provide a sustained release formulation, which is administered once or twice a day, provides a statistically equivalent pharmacokinetic parameters such as $C_{ss,max}$, $AUC_{ss}$, etc. at the plateau steady state, as compared to the rapid release tablet that is administered four times a day and has the same daily dose as the sustained release formulation, and shows a stable dissolution pattern.

In an embodiment of the present invention, in preparing a sustained release formulation containing a wax, in order to improve the compressibility of a composition therefor, copovidone, which is highly compatible to the wax, is selected as a binder, and it is granulated by the simplest and common wet granulation method. In order to improve fluidity and bulk density of the resulting granules, the solid particles obtained from the granulation are adequately treated with heat.

The resulting wax type water-insoluble matrix granules have a high inter-granular coherence. Therefore, adhesiveness between the surface of tablets and on the punch is decreased, and the consumption of a lubricant can be reduced. This facilitates the tabletting in practical production. Further, tablets with a high quality can be produced using a high speed tabletting machine with an average compression rate of 3000 tablets/min or above, and sustained release water-insoluble matrix tablets with a constant dissolution rate can be produced.

The matrix type sustained release solid formulation according to the present invention releases the drug slowly through the following mechanisms:

(1) The drug is dispersed in the matrix comprising the wax type excipient and copovidone. The wax type excipient, a hydrophobic excipient, controls penetration of the dissolution solution. Further, when manufactured into a tablet, the high coherence between wax and copovidone results in decreased porosity within the matrix and, thus, retards penetration of the dissolution medium and release of the drug.

(2) The granules comprising the wax type excipient are adequately treated with heat, so that the wax is melted and penetrates into the matrix, that is, fills the void in the matrix, which results in decreased porosity. Moreover, the wax is melted on the surface of the granules, giving a coating effect to delay the dissolution.

Further, compressibility and fluidity of the granules are improved, and adhesiveness is decreased through the following mechanisms, ultimately to facilitate the practical production:

(1) By preparing granules using a wax type excipient and copovidone, which has high compressibility and plasticity, inter-granular coherence and plasticity are improved, to prevent capping and laminating.

(2) The prepared granules are adequately heat treated to provide adequate bulk density and surface coating effect with the wax, thereby to further improve fluidity.

The formulation according to the present invention is characterized by slowly releasing the drug effectively through controlled pores therein, while retaining its appearance without any changes such as apparent disintegration over 12 or 24 hours.

The solid formulation according to the present invention may be of any form, without special limitation thereon.

Preferably, it is prepared as tablets or capsules, most preferably as tablets. The process for preparing a tablet is not particularly limited. Preferably, wet granulation, dry granulation or direct compression is employed. Most preferably, wet granulation is employed.

The present invention can also be applied to any water-soluble or water-insoluble active ingredient adequate to be manufactured into and used as a sustained release solid formulation. In the light of in-vivo pharmacokinetics, the drugs belonging to BCS classes I and II are more preferred.

Examples of the active ingredients, to which the present invention can be applied, include the followings:

analgesics such as hydromorphone, morphine, diamorphine, fentanyl, alfentanil, oxycodone, flurbiprofen, diclofenac, ketoprofen aceclofenac, and the like;

anti-allergic agents such as pheniramine, dimethindene, terfenadine, astemizole, tritoqualine, loratadine, doxylamine, mequitazine, dexchlorpheniramine, triprolidine, oxatomide, and the like;

blood pressure depressants such as doxazosin, prazosin, alprenolol, atenolol, metoprolol, bupranolol, penbutolol, propranolol, esmolol, bisoprolol, celiprolol, sotalol, metipranolol, nadolol, oxprenolol, captopril, ramipril, fosinopril, cilazapril, enalapril, and the like;

antibiotics such as amoxicillin, ampicillin, bacampicillin, piperacillin, pivampicillin, cloxacillin, penicillin V, flucloxacillin, erythromycin, metronidazole, clindamycin, trimethoprim, neomycin, cefaclor, cefadroxil, cefixime, cefpodoxime, cefuroxine, cephalexin, cefradin, and the like;

bronchodilators or antiasthmatics such as pirbuterol, orciprenaline, terbutaline, fenoterol, clenbuterol, salbutamol, procaterol, theophylline, choline theophyllinate, theophylline-ethylenediamine, and the like;

antiarrhythmics such as viquidil, procainamide, mexiletine, tocamide, propafenone, ipratropium, and the like;

central nervous system drugs such as tranylcypromide, clomipramine, maprotiline, doxepin, opipramol, amitriptyline, desipramine, imipramine, fluoroxamine, fluoxetine, paroxetine, trazodone, haloperidol, pipamperone, pimozide, sulpiride, fenetylline, methylphenidate, trifluoperazine, thioridazine, oxazepam, lorazepam, bromoazepam, alprazolam, divalproex, venlafaxine, bupropion, diazepam, clobazam, buspirone, piracetam, and the like;

cell growth inhibitors or metastasis inhibitors such as melphalan, cyclophosphamide, trofosfamide, chlorambucil, lomustine, busulfan, prednimustine, fluorouracil, methotrexate, mercaptopurine, thioguanine, hydroxycarbamide, altretamine, procarbazine, and the like;

antimigraines such as lisuride, methysergide, dihydroergotamine, ergotamine, pizotifen, and the like;

gastrointestinal drugs such as cimetidine, famotidine, ranitidine, roxatidine, pirenzipine, omeprazole, misoprostol, proglumide, cisapride, bromopride, metoclopramide, and the like;

oral antidiabetics such as tolbutamide, glibenclamide, glipizide, gliquidone, glibornuride, tolazamide, acarbose, metformin, and the like;

urinary incontinence drugs such as tolterodine, oxybutynin, trospium, propiverine, darifenacin, solifenacin, and the like;

pharmaceutically acceptable salts or esters thereof; and a combination of two or more thereof.

Preferably, the present invention may be applied to an analgesic, particularly oxycodone or a pharmaceutically acceptable salt thereof, especially, oxycodone hydrochloride.

When preparing the solid formulation, especially a tablet, in order to more adequately control the dissolution rate of the drug, it is preferred that the drug is coated with a hydrophobic carrier, for example, an oil such as vegetable oil, mineral oil and synthetic oil, a lipophilic surfactant having an HLB (hydrophilic-lipophilic balance) value less than 6, a phospholipid lecithin or a mixture thereof, and is adsorbed with an adsorbent. Preferably, the hydrophobic carrier is used at an amount of 1 to 10 parts by weight, based on 100 parts by weight of the drug. As the adsorbent, colloidal silicon dioxide, talc, metallic salt of stearic acid, etc. may be used.

Preferably, the adsorbent is used at an amount of 50 to 150 parts by weight, based on 100 parts by weight of the hydrophobic carrier.

As used herein, the wax type excipient refers to a hydrophobic fusible excipient encompassing wax-like lipid excipient, wax, and the like. The wax type excipient that can be used in the present invention may be at least one selected from a glyceryl fatty acid ester or a fatty acid ester.

Specific examples of the glyceryl fatty acid ester include glyceryl palmitostearate, glyceryl behenate, glyceryl stearate, glyceryl oleate, glyceryl myristate, and the like.

Specific examples of the fatty acid ester include cetyl palmitate, cetyl caprate, stearyl palmitate, stearyl stearate, and the like. In a most preferred embodiment of the present invention, glyceryl palmitostearate or glyceryl behenate is used. The glyceryl palmitostearate under the trade name of Precirol® ATO 5 (Gatteffosse, France) is a wax type lipid excipient with a relatively low melting point of approximately 56° C. and an HLB value of 2. The glyceryl behenate under the trade name of Compritol® 888 ATO (Gatteffosse, France) has a relatively low melting point of approximately 70° C. and an HLB value of 2. This is a natural compound serving not only as a lubricant but also as an excipient for use in the manufacture of sustained release formulations. In the present invention, Compritol mainly serves to control release.

In the present invention, the wax type excipient may be used alone or in combination of two or more. Preferably, the wax type excipient is included at an amount of 10 to 50 parts by weight, based on 100 parts by weight of the mixture or granules for the preparation of a solid formulation. When the wax type excipient is used at an amount exceeding 50 parts by weight, fluidity of the mixture may be decreased and severe adhesion may occur during tabletting, thereby to lower production efficiency. When it is used at an amount less than 10 parts by weight, a stable sustained release effect may not be expected. In addition, carnauba wax, beeswax, white beeswax, paraffin, microcrystalline wax, hydrogenated oil, etc. may be used as the wax type excipient.

In a preferred embodiment of the present invention, copovidone is included at an amount of 1 to 50 parts by weight, based on 100 parts by weight of the mixture or granules for the preparation of a solid formulation. Even when copovidone is used at an amount exceeding 50 parts by weight, compressibility and tabletting properties may not be improved in proportion to the used amount. When it is used at an amount less than 1 part by weight, it is difficult to attain improved compressibility and fluidity.

The sustained release solid formulation according to the present invention may be prepared by a process comprising the following steps:
i) mixing a drug with a wax type excipient to prepare a mixture or granules;
ii) heating the mixture or granules of step i) to a temperature at which the wax type excipient can be melted, and then cooling the heated mixture or granules; and
iii) compressing or filling into a capsule the mixture or granules of step ii),
wherein copovidone is added in any of steps i), ii) and iii) as a binder.

In step i), for more adequate release control, the drug is coated with a liquid or semisolid hydrophobic carrier, for example, an oil such as vegetable oil, mineral oil and synthetic oil, an amphoteric surfactant of lipophilic property having an HLB value less than 6, a phospholipid lecithin or a mixture thereof, directly or in a mixture with a small amount of ethanol and the ethanol is then removed, for example, at 50° C. Subsequently, the drug is adsorbed with an adsorbent, for example, colloidal silicon dioxide, talc or a mixture thereof.

During the preparation of the mixture or granules, in addition to the wax type excipient, other excipients commonly used in the preparation of solid formulations, for example, lactose and calcium hydrogen phosphate may be used. In the preparation of granules, the methods commonly used in the art, including wet granulation using water or ethanol, dry granulation, and the like may be used.

In step ii), the composition prepared in the step i) is heated at a temperature at which the wax type excipient can be melted, particularly at a temperature higher than the melting point of the wax type excipient, more particularly at a temperature 1 to 10° C. higher than the melting point of the wax type excipient, for 30 minutes to 2 hours. When the heating temperature is too high or the heating time is too long, the granules may be aggregated, and so the aggregated granules must be pulverized again and a constant dissolution may not be obtained.

In step iii), the prepared composition is manufactured into a tablet or filled in a capsule. When manufacturing a tablet by direct compression, an excipient for direct compression such as lactose, spray-dried lactose, microcrystalline cellulose, calcium hydrogen phosphate, etc. may be used together, as is well known in the pharmaceutical field.

In the present invention, the binder, copovidone, may be in added in any of steps i) to iii). It may be mixed with the wax to form the mixture or granules, added after the granulation and subjected to heat treatment, or added after the heat treatment during tabletting. Most preferably, it is mixed with the wax and prepared into granules.

Further, in an embodiment of the present invention, any common release control agents known in the art, for example, at least one selected from polyvinyl acetate, polyoxyethylene-polyoxypropylene block copolymer, poloxamer, polyethylene oxide, hydroxypropylalkylcellulose, hydroxyalkylcellulose, sodium alginate, xanthan gum, locust bean gum, ammonio methacrylate copolymer, anionic copolymer of methacrylic acid and methacrylic acid methyl or ethyl ester, hydroxypropylmethylcellulose acetyl succinate, hydroxypropylmethylcellulose phthalate and carboxyvinyl polymer (Carbopol®) may be used. The formulation of the present invention may be prepared into sugar coated tablet, film-coated tablet, etc. using a coating agent that can be commonly used in the pharmaceutical field.

Hereinafter, the present invention will be specifically described with reference to the following examples, which are provided only for the better understanding of the present invention, but should not be construed to limit the scope of the present invention in any manner.

Example 1

Preparation of Sustained Release Formulations

Oxycodone hydrochloride and Labrafil®M 1944 CS were mixed homogeneously and adsorbed with colloidal silicon dioxide. To the drug pre-treated as described above were successively added Compritol® 888 ATO (glyceryl behenate), calcium hydrogen phosphate and copovidone, and the mixture was wet granulated in ethanol. The obtained granules were dispersed on a broad plate and heat treated in an oven of 75° C. for 1 hour. Then, the granules were cooled to room temperature and passed through a sieve of No. 20. Talc and magnesium stearate were added thereto, and a punch having a diameter of 7.2 mm was used to prepare each 125 mg of oxycodone hydrochloride sustained release tablets. The ingredients of each unit tablet are listed in Table 1.

TABLE 1

| Example 1 | mg/tablet | weight % |
|---|---|---|
| Oxycodone hydrochloride | 40 | 32.0 |
| Labrafil ® M 1944 CS | 2 | 1.6 |
| Colloidal silicon dioxide | 2 | 1.6 |
| Calcium hydrogen phosphate | 30 | 24.0 |
| Compritol ® 888 ATO | 40 | 32.0 |
| Copovidone | 7.25 | 5.8 |
| Talc | 2.5 | 2.0 |
| Magnesium stearate | 1.25 | 1.0 |
| Total | 125 | 100 |

Examples 2 to 5

Preparation of Sustained Release Formulations

Oxycodone hydrochloride, Compritol® 888 ATO (glyceryl behenate), calcium hydrogen phosphate and copovidone were mixed together, and the mixture was wet granulated in ethanol.

The obtained granules were dispersed on a broad plate and heat treated in an oven of 75° C. for 1 hour. Then, the heated granules were cooled to room temperature and passed through a sieve of No. 20.

The prepared granules had suitable volume and fluidity for the manufacture of tablets, with the bulk density of approximately 0.56 g/cm³ and the angle of repose of approximately 30 degrees. To the mixture were added talc and magnesium stearate, and a punch having a diameter of 7.2 mm was used to prepare each 125 mg of oxycodone hydrochloride sustained release tablets. The ingredients of each unit tablet are listed in Table 2.

Test Example 1

Dissolution Test

Drug dissolution profiles from the oxycodone hydrochloride sustained release formulations prepared in Examples 1 to 5 were measured by USP Dissolution Test #1 (rotating basket method). 900 mL of pH 6.8 phosphate buffer was used as a test solution, and rotation speed was 100 rpm.

At a given time, the dissolution solution was taken and filtered, and the content of oxycodone hydrochloride remaining in the filtrate was determined. The result is given in the following Table 3.

TABLE 3

| | Dissolution rate (%) at different times | | | | |
|---|---|---|---|---|---|
| Time (hr) | Example 1 | Example 2 | Example 3 | Example 4 | Example 5 |
| 0.5 | 21.0 | 24.2 | 26 | 29.4 | 34.1 |
| 1 | 30.0 | 31.8 | 34.6 | 39.4 | 44.4 |
| 2 | 41.3 | 42.5 | 46.0 | 50.5 | 58.2 |
| 4 | 56.3 | 56.9 | 58.8 | 65.1 | 75.3 |
| 6 | 67.0 | 65.6 | 70.6 | 75.6 | 80.6 |
| 8 | 75.1 | 73.5 | 76.4 | 84.5 | 90.6 |
| 12 | 87.0 | 84.4 | 89.4 | 94.4 | 99.4 |

The dissolution test was also carried out for commercially available OxyContin sustained release tablet (40 mg/tablet, Mundipharma). The dissolution test result for the tablet prepared in Example 5 and the commercially available tablet is illustrated in FIG. 1.

Examples 6 to 9

Preparation of Sustained Release Formulations

Oxycodone hydrochloride, Compritol® 888 ATO (glyceryl behenate), calcium hydrogen phosphate, lactose and copovidone were mixed together, such that each tablet contained 40 mg, 30 mg, 20 mg and 10 mg of oxycodone hydrochloride, and the mixtures were wet granulated in ethanol. The resultant granules were dispersed on a broad plate and heat treated in an oven of 75° C. for 1 hour. The heated granules were cooled to room temperature and passed through a sieve of No. 20. Talc and magnesium stearate were added thereto, and a punch having a diameter of 7.2 mm was used to prepare each 125 mg of oxycodone hydrochloride sustained release tablets. The ingredients of each unit tablet are listed in Table 4.

TABLE 2

| | Example 2 | | Example 3 | | Example 4 | | Example 5 | |
|---|---|---|---|---|---|---|---|---|
| Compositions | mg/tablet | weight % | mg/tablet | weight % | mg/tablet | weight % | mg/tablet | weight % |
| Oxycodone hydrochloride | 40 | 32.0 | 40 | 32.0 | 40 | 32.0 | 40 | 32.0 |
| Compritol ® 888 ATO | 40 | 32.0 | 35 | 28.0 | 30 | 24.0 | 25 | 20.0 |
| Calcium hydrogen phosphate | 31.25 | 25.0 | 36.25 | 29.0 | 41.25 | 33.0 | 46.25 | 37.0 |
| Copovidone | 10 | 8.0% | 10 | 8.0% | 10 | 8.0% | 10 | 8.0% |
| Talc | 2.5 | 2.0% | 2.5 | 2.0% | 2.5 | 2.0% | 2.5 | 2.0% |
| Magnesium stearate | 1.25 | 1.0% | 1.25 | 1.0% | 1.25 | 1.0% | 1.25 | 1.0% |
| Total | 125 | 100% | 125 | 100% | 125 | 100% | 125 | 100% |

TABLE 4

| Compositions | Example 6 mg/tablet | Example 6 weight % | Example 7 mg/tablet | Example 7 weight % | Example 8 mg/tablet | Example 8 weight % | Example 9 mg/tablet | Example 9 weight % |
|---|---|---|---|---|---|---|---|---|
| Oxycodone hydrochloride | 40 | 32.0% | 30 | 24.0% | 20 | 16.0% | 10 | 8.0% |
| Compritol ® 888 ATO | 30 | 24.0% | 30 | 24.0% | 30 | 24.0% | 30 | 24.0% |
| Calcium hydrogen phosphate | 28.75 | 23.0% | 28.75 | 23.0% | 28.75 | 23.0% | 28.75 | 23.0% |
| Lactose | 12.5 | 10.0% | 22.5 | 18.0% | 32.5 | 26.0% | 42.5 | 34.0% |
| Copovidone | 10 | 8.0% | 10 | 8.0% | 10 | 8.0% | 10 | 8.0% |
| Talc | 2.5 | 2.0% | 2.5 | 2.0% | 2.5 | 2.0% | 2.5 | 2.0% |
| Magnesium stearate | 1.25 | 1.0% | 1.25 | 1.0% | 1.25 | 1.0% | 1.25 | 1.0% |
| Total | 125 | 100% | 125 | 100% | 125 | 100% | 125 | 100% |

Test Example 2

Dissolution Test

Drug dissolution profiles of the oxycodone hydrochloride sustained release formulations prepared in Examples 6 to 9 were measured in substantially the same manner as in Test Example 1. The result is given in the following Table 5.

TABLE 5

| | Dissolution rate (%) at different times | | | |
|---|---|---|---|---|
| Time (hr) | Example 6 | Example 7 | Example 8 | Example 9 |
| 0.5 | 27.1 | 25.4 | 28.1 | 25.3 |
| 1 | 37.7 | 35.1 | 39.9 | 33.8 |
| 2 | 51.1 | 48.5 | 52.3 | 47.5 |
| 4 | 70.7 | 62.4 | 70.1 | 64.0 |
| 6 | 79.0 | 72.6 | 84.1 | 69.7 |
| 8 | 88.1 | 80.1 | 90.0 | 79.4 |
| 12 | 97.1 | 90.1 | 94.1 | 88.2 |

Examples 10 to 13

Preparation of Sustained Release Formulations

Oxycodone hydrochloride, a wax type excipient, Precirol® ATO 5 (Gatteffosse, France), Lubritab® (JRS), Sterotex® HM or Sterotex® NF (Abitec), calcium hydrogen phosphate, lactose and copovidone were mixed together, such that each tablet contained 40 mg, 30 mg, 20 mg and 10 mg of oxycodone hydrochloride, and the mixtures were wet granulated in ethanol.

The resultant granules were dispersed on a broad plate and heat treated in an oven of 75° C. for 1 hour. The heated granules were cooled to room temperature and passed through a sieve of No. 20. Talc and magnesium stearate were added to the mixture, and a punch having a diameter of 7.2 mm was used to prepare each 125 mg of oxycodone hydrochloride sustained release tablets. The ingredients of each unit tablet are listed in Table 6.

TABLE 6

| Compositions | Example 10 mg/tablet | Example 10 weight % | Example 11 mg/tablet | Example 11 weight % | Example 12 mg/tablet | Example 12 weight % | Example 13 mg/tablet | Example 13 weight % |
|---|---|---|---|---|---|---|---|---|
| Oxycodone hydrochloride | 20 | 16.0% | 20 | 16.0% | 20 | 16.0% | 20 | 16.0% |
| Precirol ® ATO 5 | 30 | 24.0% | — | — | — | — | — | — |
| Lubritab ® | — | — | 30 | 24.0% | — | — | — | — |
| Sterotex ® HM | — | — | — | — | 30 | 24.0% | — | — |
| Sterotex ® NF | — | — | — | — | — | — | 30 | 24.0% |
| Lactose | 20 | 16.0% | 20 | 16.0% | 20 | 16.0% | 20 | 16.0% |
| Calcium hydrogen phosphate | 41.25 | 33.0% | 41.25 | 33.0% | 41.25 | 33.0% | 41.25 | 33.0% |
| Copovidone | 10 | 8.0% | 10 | 8.0% | 10 | 8.0% | 10 | 8.0% |
| Talc | 2.5 | 2.0% | 2.5 | 2.0% | 2.5 | 2.0% | 2.5 | 2.0% |
| Magnesium stearate | 1.25 | 1.0% | 1.25 | 1.0% | 1.25 | 1.0% | 1.25 | 1.0% |
| Total | 125 | 100% | 125 | 100% | 125 | 100% | 125 | 100% |

Test Example 3

Dissolution Test

Drug dissolution profiles of the oxycodone hydrochloride sustained release formulations prepared in Examples 10 to 13 were measured in substantially the same manner as in Test Example 1. The result is given in the following Table 7.

TABLE 7

| | Dissolution rate (%) at different times | | | |
|---|---|---|---|---|
| Time (hr) | Example 10 | Example 11 | Example 12 | Example 13 |
| 0.5 | 22.0 | 32.0 | 36.6 | 30.7 |
| 1 | 31.4 | 43.6 | 48.4 | 41.7 |
| 2 | 45.9 | 60.0 | 62.0 | 57.3 |
| 4 | 66.2 | 78.0 | 78.7 | 75.6 |
| 6 | 80.4 | 88.1 | 88.0 | 87.7 |
| 8 | 88.6 | 93.4 | 96.7 | 93.3 |
| 12 | 96.6 | 97.0 | 98.7 | 97.3 |

Example 14 to 16

Preparation of Sustained Release Formulation

Oxycodone hydrochloride, Compritol® 888 ATO (glyceryl behenate), calcium hydrogen phosphate, lactose and copovidone were mixed together, such that each tablet contained 20 mg, 30 mg and 40 mg of oxycodone hydrochloride, and the mixture were wet granulated in ethanol. The resultant granules were dispersed on a broad plate and heat treated in an oven of 75° C. for 1 hour. The heated granules were cooled to room temperature and passed through a sieve of No. 20. Talc and magnesium stearate were added to the mixture, and a punch having a diameter of 7.2 mm was used to prepare each 125 mg of oxycodone hydrochloride sustained release tablets. The ingredients of each unit tablet are listed in Table 8.

TABLE 8

| | Example 14 | | Example 15 | | Example 16 | |
|---|---|---|---|---|---|---|
| Compositions | mg/tablet | weight % | mg/tablet | weight % | mg/tablet | weight % |
| Oxycodone hydrochloride | 20 | 13.3% | 30 | 20.0% | 40 | 26.7% |
| Compritol ® 888 ATO | 48 | 32.0% | 54 | 36.0% | 60 | 40.0% |
| Calcium hydrogen phosphate | 52 | 34.7% | 36 | 24.0% | 20 | 13.3% |
| Lactose | 10 | 6.7% | 10 | 6.7% | 10 | 6.7% |
| Copovidone | 15 | 10% | 15 | 10.0% | 15 | 10.0% |
| Talc | 3 | 2.0% | 3 | 2.0% | 3 | 2.0% |
| Magnesium stearate | 2 | 1.3% | 2 | 1.3% | 2 | 1.3% |
| Total | 150 | 100% | 150 | 100% | 150 | 100% |

Test Example 4

Dissolution Test

Drug dissolution profiles of the oxycodone hydrochloride sustained release formulations prepared in Examples 14 to 16 were measured in substantially the same manner as in Test Example 1. The result is given in the following Table 9.

TABLE 9

| | Dissolution rate (%) at different times | | |
|---|---|---|---|
| Time (hr) | Example 14 | Example 15 | Example 16 |
| 1 | 19.3 | 19.8 | 18.5 |
| 2 | 22.5 | 22.6 | 21.9 |
| 3 | 26.9 | 27.2 | 26.3 |
| 4 | 30.7 | 31.4 | 30.5 |
| 6 | 37.2 | 37.7 | 36.3 |
| 8 | 42.5 | 43.4 | 41.5 |
| 10 | 48.4 | 48.7 | 47.3 |
| 14 | 60.0 | 56.1 | 55.9 |
| 16 | 62.6 | 59.6 | 59.4 |
| 18 | 67.7 | 64.0 | 63.8 |
| 20 | 72.1 | 68.3 | 68.0 |
| 24 | 82.2 | 80.9 | 76.7 |

INDUSTRIAL APPLICABILITY

The present invention provides a mixture or granules for the preparation of a sustained release solid formulation, which has increased compressibility and fluidity and reduced adhesiveness and can be produced easily using a high speed tabletting machine. The prepared solid formulation exhibits a superior sustained release effect over a long period of time.

Although the preferred embodiments of the present invention have been disclosed for illustrative purposes, those skilled in the art will appreciate that various modifications, additions and substitutions are possible, without departing from the scope and spirit of the invention as disclosed in the accompanying drawings.

The invention claimed is:

1. A sustained release solid oral formulation comprising oxycodone or oxycodone hydrochloride that is first coated with a liquid or semisolid hydrophobic carrier selected from the group consisting of vegetable oil, mineral oil, synthetic oil, amphoteric surfactant having an HLB (hydrophilic-lipophilic balance) value less than 6, phospholipid lecithin and a mixture thereof, and is then adsorbed with an adsorbent selected from the group consisting of colloidal silicon dioxide, talc and a mixture thereof, in a water-insoluble matrix, wherein the water-insoluble matrix comprises copovidone as a binder and a wax type excipient selected from the group consisting of glyceryl fatty acid ester and hydrogenated oil, wherein the matrix has a void and/or surface, the void being filled or the surface being coated with the wax type excipient and the copovidone which have been melted, cooled and solidified, wherein the sustained release solid oral formulation achieves a linear release rate of oxycodone or oxycodone hydrochloride for a period of at least 12 hours.

2. The sustained release solid oral formulation as set forth in claim 1, which is prepared by a method comprising:
   i) coating oxycodone or oxycodone hydrochloride with a liquid or semisolid hydrophobic carrier selected from the group consisting of vegetable oil, mineral oil, synthetic oil, amphoteric surfactant having an HLB (hydrophilic-lipophilic balance) value less than 6, phospholipid lecithin and a mixture thereof, and adsorbing an adsorbent selected from the group consisting of colloidal silicon dioxide, talc and a mixture thereof to form coated oxycodone or oxycodone hydrochloride;
   ii) mixing the coated oxycodone or oxycodone hydrochloride of step i) with copovidone as a binder and a wax type excipient selected from the group consisting of glyceryl fatty acid ester and hydrogenated oil as materials forming the matrix to prepare granules;
   iii) heating the granules of step ii) to a temperature at which the wax type excipient and copovidone can be melted to prepare a matrix, wherein the matrix has a void and/or surface, the void being filled or the surface being coated with the wax type excipient and the copovidone in the matrix; and
   iv) cooling the product of step iii).

3. The formulation as set forth in claim 1, wherein the glyceryl fatty acid ester is selected from the group consisting of glyceryl palmitostearate and glyceryl behenate.

4. The formulation as set forth in claim 2, wherein the wax type excipient is included at an amount of 10 to 50 parts by weight, based on 100 parts by weight of the granules.

5. The formulation as set forth in claim 2, wherein copovidone is included at an amount of 1 to 50 parts by weight, based on 100 parts by weight of the granules.

6. The formulation as set forth in claim 1, wherein the hydrophobic carrier is used at an amount of 1 to 10 parts by weight based on 100 parts by weight of oxycodone or oxycodone hydrochloride, and the adsorbent is used at an amount of 50 to 150 parts by weight based on 100 parts by weight of the hydrophobic carrier.

7. The formulation as set forth in claim 1, which further comprises a release control agent selected from the group consisting of alkyl cellulose, polyvinyl acetate, polyoxyethylene-polyoxypropylene block copolymer, polyethylene oxide, hydroxypropylalkylcellulose, hydroxyalkylcellulose, sodium alginate, xanthan gum, locust bean gum, ammonio methacrylate copolymer, anionic copolymer of methacrylic acid and methacrylic acid methyl or ethyl ester, hydroxypropylmethylcellulose acetyl succinate, hydroxypropylmethylcellulose phthalate, carboxyvinyl polymer and a mixture thereof.

8. A method of preparing a sustained release solid oral formulation as set forth in claim 1, which comprises:
   i) mixing oxycodone or oxycodone hydrochloride with a wax type excipient to prepare a mixture or granules;
   ii) heating the mixture or granules of step i) to a temperature at which the wax type excipient can be melted, and then cooling the heated mixture or granules; and
   iii) compressing or filling in a capsule the mixture or granules of step ii), wherein copovidone is added in any of steps i), ii) and iii).

9. The method as set forth in claim 8, wherein, in step ii), the heating is performed at a temperature higher than the melting point of the wax type excipient for 0.5 to 2 hours.

10. The method as set forth in claim 9, wherein, in step ii), the temperature is 1 to 10° C. higher than the melting point of the wax type excipient.

* * * * *